United States Patent
Sullivan et al.

(10) Patent No.: US 11,984,217 B2
(45) Date of Patent: May 14, 2024

(54) METHOD AND APPARATUS FOR PROCESSING HISTOLOGICAL IMAGE CAPTURED BY MEDICAL IMAGING DEVICE

(71) Applicant: KOH YOUNG TECHNOLOGY INC., Seoul (KR)

(72) Inventors: Kenneth Mark Sullivan, San Diego, CA (US); Jin Man Kang, San Diego, CA (US)

(73) Assignee: KOH YOUNG TECHNOLOGY INC., Seoul (KR)

( * ) Notice: Subject to any disclaimer, the term of this patent is extended or adjusted under 35 U.S.C. 154(b) by 334 days.

(21) Appl. No.: 16/487,636

(22) PCT Filed: Feb. 21, 2018

(86) PCT No.: PCT/KR2018/002118
§ 371 (c)(1),
(2) Date: Aug. 21, 2019

(87) PCT Pub. No.: WO2018/155898
PCT Pub. Date: Aug. 30, 2018

(65) Prior Publication Data
US 2020/0035350 A1 Jan. 30, 2020

Related U.S. Application Data

(60) Provisional application No. 62/563,751, filed on Sep. 27, 2017, provisional application No. 62/461,490, filed on Feb. 21, 2017.

(51) Int. Cl.
*G16H 30/40* (2018.01)
*G06N 3/08* (2023.01)
(Continued)

(52) U.S. Cl.
CPC ............... *G16H 30/40* (2018.01); *G06N 3/08* (2013.01); *G06N 20/00* (2019.01); *G06T 11/001* (2013.01);
(Continued)

(58) Field of Classification Search
None
See application file for complete search history.

(56) References Cited

U.S. PATENT DOCUMENTS

| 7,545,965 B2 | 6/2009 | Suzuki et al. |
| 2010/0111396 A1 | 5/2010 | Boucheron |

(Continued)

FOREIGN PATENT DOCUMENTS

| CN | 102665526 | 9/2012 |
| JP | 2011-104016 A | 6/2011 |

(Continued)

OTHER PUBLICATIONS

Baz, Ayman El-, et al. "Computer-Aided Diagnosis Systems for Lung Cancer: Challenges and Methodologies." International Journal of Biomedical Imaging (2013): NA. ProQuest. Web. Aug. 23, 2023. (Year: 2013).*

(Continued)

*Primary Examiner* — Lena Najarian
(74) *Attorney, Agent, or Firm* — KILE PARK REED & HOUTTEMAN PLLC (57) ABSTRACT

A method for processing one or more histological images captured by a medical imaging device is disclosed. In this method, the histological image is received, and target regions each of which corresponds to a candidate type of tissue are identified based on a predictive model associating one more sample histological images with one or more sample target histological images. One or more display (Continued)

characteristics associated with the identified at least one target histological image is applied to the histological image.

7 Claims, 7 Drawing Sheets (51) Int. Cl.
  *G06N 20/00* (2019.01)
  *G06T 11/00* (2006.01)
  *G16H 50/20* (2018.01)
  *G16H 50/50* (2018.01)
  *G16H 30/20* (2018.01)
  *G16H 70/00* (2018.01)

(52) U.S. Cl.
  CPC ............. *G16H 50/20* (2018.01); *G16H 50/50* (2018.01); *G06T 2210/41* (2013.01); *G16H 30/20* (2018.01); *G16H 70/00* (2018.01)

(56) References Cited

U.S. PATENT DOCUMENTS

| | | | |
|---|---|---|---|
| 2012/0082362 A1* | 4/2012 | Diem | A61B 5/418 382/133 |
| 2012/0220840 A1 | 8/2012 | Morita et al. | |
| 2012/0237109 A1 | 9/2012 | Rajpoot et al. | |
| 2013/0034263 A1* | 2/2013 | Ding | G06K 9/6269 382/103 |
| 2013/0230230 A1 | 9/2013 | Ajemba et al. | |
| 2013/0317369 A1 | 11/2013 | Bryant-Greenwood et al. | |
| 2014/0270457 A1 | 9/2014 | Bhargava | |
| 2014/0270495 A1* | 9/2014 | Tu | G06F 18/2155 382/160 |
| 2015/0238148 A1 | 8/2015 | Georgescu et al. | |
| 2015/0269314 A1 | 9/2015 | Kopriva et al. | |
| 2018/0121626 A1* | 5/2018 | Abedini | G06T 7/0014 |

FOREIGN PATENT DOCUMENTS

| | | | | |
|---|---|---|---|---|
| WO | WO-2009058915 A1 * | 5/2009 | ........... | G06K 9/4619 |
| WO | 2016092394 A1 | 6/2016 | | |

OTHER PUBLICATIONS

Extended European Search Report, corresponding to European Application No./Patent No. 18756616.1, dated Dec. 1, 2020.
International Search Report for International Application No. PCT/KR2018/002118, dated Jun. 4, 2018.
Written Opinion for International Application No. PCT/KR2018/002118, dated Jun. 4, 2018.
Japanese Office Action corresponding to Japanese Application No. 2019-566558, dated Apr. 5, 2022.
Korean Office Action with English translation for Korean Patent Application No. 10-2019-7027374, dated May 4, 2023.
Chinese Office Action, with complete English Translation, for Chinese Application No. 2018800128054, dated Mar. 22, 2023.

* cited by examiner

METHOD AND APPARATUS FOR PROCESSING HISTOLOGICAL IMAGE CAPTURED BY MEDICAL IMAGING DEVICE

This application is based upon and claims the benefit of priority from prior U.S. Provisional Patent Application No. 62/461,490, filed Feb. 21, 2017, and U.S. Provisional Patent Application No. 62/563,751, filed Sep. 27, 2017, the entire contents of which are incorporated herein by reference.

TECHNICAL FIELD

The present disclosure relates generally to processing a histological image for display, and more specifically, to generating a modified image of the histological image using a semi-supervised learning model.

BACKGROUND ART

In histology, H&E (hematoxylin and eosin) stain has been widely used in medical diagnosis. For example, for examining a suspected lesion such as a cancer in a body of a patient, a doctor may obtain a sample of the suspected lesion and conduct a predetermined procedure for generating a micrograph of H&E stain. The doctor may then view the micrograph of H&E stain under a microscope to diagnose a disease of the patient. To obtain a micrograph of H&E stain, a sample of a suspected lesion from a patient is typically sent to a histology laboratory. In addition, a series of predetermined procedures are performed for generating a micrograph of H&E stain. Such procedures usually take one or more days for obtaining the micrograph of H&E stain. In some cases, to provide timely treatment of a disease, a prompt diagnosis of the disease may be required during surgical operation. However, according to the above procedures, a disease for the suspected lesion may not be diagnosed instantly during the operation.

Meanwhile, images such as CT (Computer Tomography), MRI (Magnetic Resonance Imaging) micrographs, etc. may be captured and used for firmly diagnosing a potential patient. However, capturing such a micrographic image may be relatively expensive for the potential patient. In addition, such CT and MRI devices may be too huge to be used for capturing a portion of a human body during an operation. That is, the devices may not be suitable for being located in or moving to an operating room during an operation.

For instant and quick diagnosis purposes, images with a relatively low quality-captured by a medical imaging device such as an OCT (Optical Coherence Tomography) device, etc. have been used for locating a suspected lesion in a patient. Such an image can be obtained cheaper than CT and/or MRI micrographs and can be generated more rapidly than the micrographs of H&E stain. However, such an image may not be provided with visibility suitable for accurately diagnosing a disease of one or more types of tissue in the image.

DISCLOSURE OF INVENTION

Technical Problem

Embodiments disclosed in the present disclosure relate to generate a modified image of a histological image captured by a medical imaging device using a predictive model that may be a semi-supervised learning model.

Solution to Problem

According to one aspect of the present disclosure, a method, performed by a computer, for processing one or more histological images captured by a medical imaging device is disclosed. In this method, each of the histological images including at least one type of tissue is received, and at least one candidate type of tissue in each of the histological images is determined by a first autoencoder. At least one target region corresponding to the at least one candidate type of tissue in the histological image is identified by the first autoencoder. At least one target histological image corresponding to the target region in each of the histological images is identified based on a predictive model associating one or more sample histological images with one or more sample target histological images. One or more display characteristics associated with the identified target histological image or images is applied to the histological image. This disclosure also describes a device and a computer-readable medium relating to this method.

Advantageous Effects of Invention

One aspect of the present disclosure is related to a method, performed by a computer, for processing a histological image captured by a medical imaging device, the method comprising: receiving the histological image including at least one type of tissue; determining, by a first autoencoder, a candidate type of tissue in the histological image; identifying, by the first autoencoder, a target region corresponding to the candidate type of tissue in the histological image; identifying at least one target histological image corresponding to the target region in the histological image based on a predictive model associating one or more sample histological images with one or more sample target histological images; and applying one or more display characteristics associated with the identified at least one target histological image to the histological image. The method may further include generating a modified image of the histological image including the applied display characteristics.

In one embodiment, the predictive model may include a first set of patches in each of the sample histological images and a second set of patches in each of the sample target histological images, wherein the first set of patches is associated with the second set of patches in the predictive model, and wherein applying the one or more display characteristics includes modifying a plurality of patches in the received histological image based on the second set of patches in the identified at least one target histological image.

In one embodiment, identifying the target region corresponding to the candidate type of tissue may include identifying a plurality of regions comprising the target region in the histological image, wherein the predictive model includes a first set of regions in each of the sample histological images and a second set of regions in each of the sample target histological images, wherein the first set of regions is associated with the second set of regions in the predictive model, and wherein applying one or more display characteristics includes modifying the plurality of regions in the received histological image based on the second set of regions in the identified at least one target histological image.

In one embodiment, a first unsupervised learning model may be generated by training the first autoencoder based on a first set of sample histological images. In one embodiment, the predictive model may be generated based on the first unsupervised learning model and a second unsupervised learning model, and the second unsupervised learning model may be generated by training a second set of sample target histological images. In one embodiment, one or more anatomical locations of M sample histological images in the first set of sample histological images may be aligned to match one or more anatomical locations of N sample target histological images in the second set of sample target histological images, M and N being positive integers. In one embodiment, the predictive model may include data regarding one or more features indicative of one or more display characteristics and is trained by associating one or more features from the N sample target histological images with one or more features from the M sample histological images.

In one embodiment, the histological image captured by the medical imaging device may include one or more histological images of a target structure, and the target structure may have a depth of 2 to 4 mm from a visible surface. In one embodiment, the first unsupervised learning model may be trained based on one or more features associated with the target region in the histological image. In one embodiment, each of the first unsupervised learning model, the second unsupervised learning model, and the predictive model may include a multilayer model defined by one or more model hyperparameters and one or more weights of an artificial neural network.

One aspect of the present disclosure is related to an image processing device for processing a histological image captured by a medical imaging device, the device comprising: a first autoencoder configured to: receive the histological image including at least one type of tissue; determine a candidate type of tissue in the histological image; and identify a target region corresponding to the candidate type of tissue in the histological image; and an image generating unit configured to: identify at least one target histological image corresponding to the target region in the histological image based on a predictive model associating one or more sample histological images with one or more sample target histological images; and apply one or more display characteristics associated with the identified at least one target histological image to the histological image.

In one embodiment, the image generating unit may be further configured to generate a modified image of the histological image including the applied display characteristics. In one embodiment, the first autoencoder may be further configured to identify a plurality of regions comprising the target region in the histological image, wherein the predictive model includes a first set of regions in each of the sample histological images and a second set of regions in each of the sample target histological images, wherein the first set of regions is associated with the second set of regions in the predictive model, and wherein the image generating unit is further configured to modify the plurality of regions in the received histological image based on the second set of regions in the identified at least one target histological image.

In one embodiment, a first unsupervised learning model may be generated by training the first autoencoder based on a first set of sample histological images. In one embodiment, the predictive model may be generated based on the first unsupervised learning model and a second unsupervised learning model, and the second unsupervised learning model may be generated by training a second set of sample target histological images. In one embodiment, one or more anatomical locations of M sample histological images in the first set of sample histological images may be aligned to match one or more anatomical locations of N sample target histological images in the second set of sample target histological images, M and N being positive integers.

One aspect of the present disclosure is related to a non-transitory computer-readable storage medium comprising instructions for processing a histological image, the instructions causing a processor of a computer to perform operations comprising: receiving the histological image including at least one type of tissue; determining a candidate type of tissue in the histological image; identifying a target region corresponding to the candidate type of tissue in the histological image; identifying at least one target histological image corresponding to the target region in the histological image based on a predictive model associating one or more sample histological images with one or more sample target histological images; and applying one or more display characteristics associated with the identified at least one target histological image to the histological image.

In one embodiment, identifying the target region corresponding to the candidate type of tissue may include identifying a plurality of regions comprising the target region in the histological image, wherein the predictive model includes a first set of regions in each of the sample histological images and a second set of regions in each of the sample target histological images, wherein the first set of regions is associated with the second set of regions in the predictive model, and wherein applying one or more display characteristics includes modifying the plurality of regions in the received histological image based on the second set of regions in the identified at least one target histological image.

In one embodiment, the predictive model may include one or more features indicative of a plurality of display characteristics and may be trained by associating one or more features from N sample target histological images in a second set of sample target histological images with one or more features from M sample histological images in a first set of sample histological images, M and N being positive integers

BRIEF DESCRIPTION OF DRAWINGS

Embodiments of the inventive aspects of this disclosure will be understood with reference to the following detailed description, when read in conjunction with the accompanying drawings.

MODE FOR THE INVENTION

Reference will now be made in detail to various embodiments, examples of which are illustrated in the accompanying drawings. In the following detailed description, numerous specific details are set forth in order to provide a thorough understanding of the present subject matter. However, it will be apparent to one of ordinary skill in the art that the present subject matter may be practiced without these specific details. In other instances, well-known methods, procedures, systems, and components have not been described in detail so as not to unnecessarily obscure aspects of the various embodiments.

Figure 1:
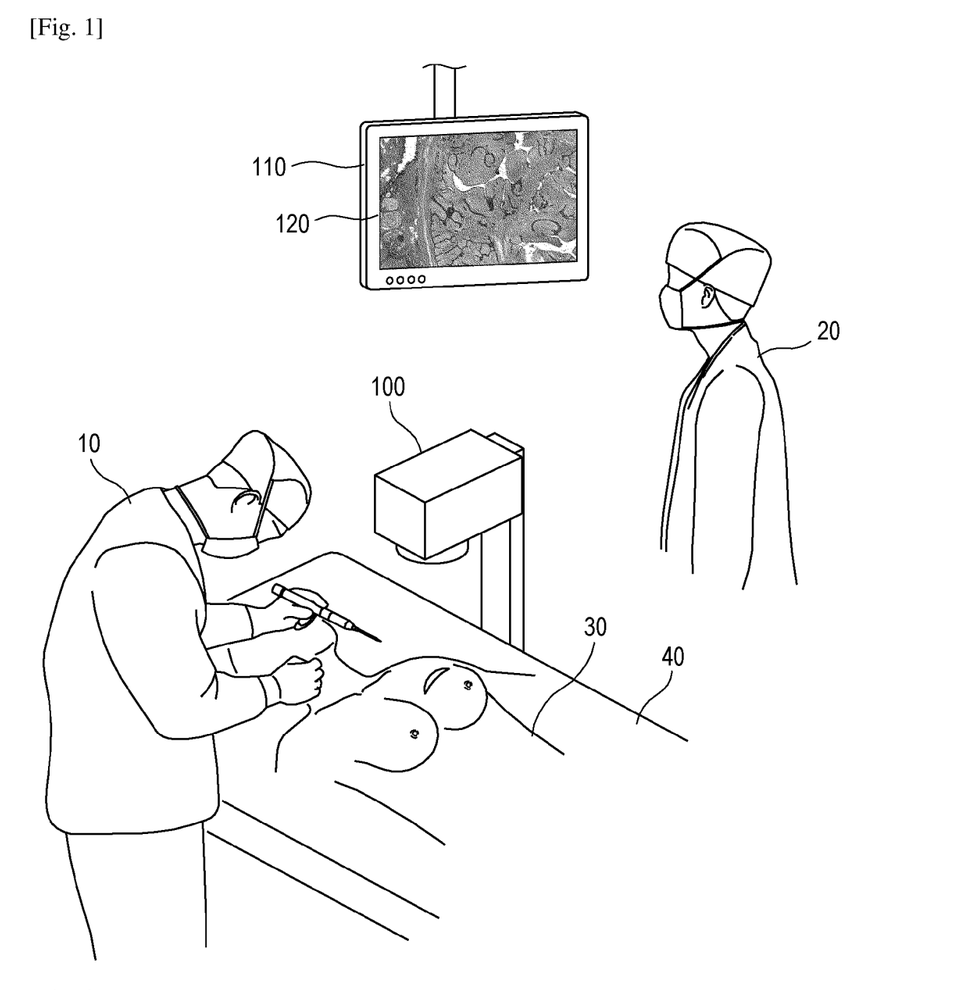
FIG. 1 depicts an operating room environment in which a medical imaging device is running during medical surgery and a modified image of a histological image captured by the medical imaging device is displayed on a display unit, according to one embodiment of the present disclosure.

FIG. 1 illustrates an operating room environment in which a medical imaging device 100 is running during medical surgery and a modified image 120 of a histological image captured by the medical imaging device 100 is displayed on a display device 110, according to one embodiment of the present disclosure. In the operating room as illustrated, doctors 10 and/or 20 may operate on a patient 30 who lies on a bed 40. In this embodiment, the doctors 10 and/or 20 may use the medical imaging device 100 to diagnose a disease or illness of the patient 30 during the surgery. For example, the medical imaging device 100 may be any type of image capturing device configured to capture a 2-dimensional or 3-dimensional histological image of a body portion such as an OCT device, an X-ray radiography device, an MRI device, a CT device, a ultrasonography or ultrasound device, an endoscopy device, a tactile imaging device, a thermography device, a nuclear medicine functional imaging device, or the like.

The medical imaging device 100 may be configured to capture or generate a histological image (e.g., M2™ image captured by an OCT device of the M2™ OCT Imaging System) including at least one type of tissue in a body portion of the patient 30. For example, if the histological image is captured by the OCT device, the histological image may be a gray-scale image. Although the medical imaging device 100 is illustrated as being fixedly installed at the bed 40 in this embodiment, the device 100 may be configured to be fixedly installed at any portion of the operating room such that it can capture an image of a body portion of the patient 30. Alternatively, the device 100 may be configured to be detachable and/or portable so that it may be located by the doctor 10 and/or 20 near an interested portion of the patient 30.

According to one embodiment, if the medical imaging device 100 is the OCT device, the medical imaging device 100 may irradiate light (e.g., laser or low-coherence light) on a body portion of the patient 30 using a light source and collect light backscattered at the body portion of the patient 30 to measure an echo time delay of the backscattered light that is captured by the medical imaging device 100. In addition, the medical imaging device 100 may be configured to identify optical coherence of the collected light. The medical imaging device 100 may generate one or more 2-dimensional (e.g., images of vertical slices) and/or 3-dimensional histological images (e.g., 3-dimensional tomogram) indicative of at least one type of tissue in the body portion by, for example, measuring the echo time delay and/or determining the optical coherence of light. The 2-dimensional histological images or 3-dimensional histological images including at least one type of tissue may have a target structure with a predetermined depth (e.g., about 2 to 4 mm) from a visible surface. In one embodiment, the medical imaging device 100 may be configured to generate 2-dimensional histological images indicative of a portion of the target structure by cropping or slicing one or more 3-dimensional histological images in any direction. In one embodiment, the medical imaging device 100 may be configured to generate one or more 3-dimensional histological images of the body portion in the patient 30 based on the 2-dimensional histological images.

Upon generating the 3-dimension histological images or 2-dimensional histological images for the body portion in the patient 30, the generated histological image may be provided to an image processing device (not shown), which will be described in detail later with reference to FIG. 3. The image processing device may be configured to receive and/or process the histological image including the plurality of types of tissue. In one embodiment, upon receiving the histological image from the medical imaging device 100, the image processing device may process the histological image to generate a modified image 120 of the histological image.

Figure 2:
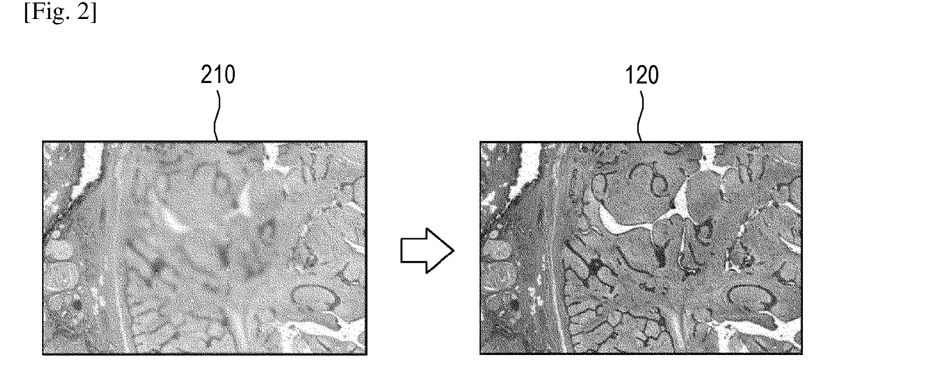
FIG. 2 is a flow diagram for identifying at least one target histological image corresponding to a target region in a histological image based on a predictive model and generating a modified image of the histological image by applying one or more display characteristics associated with the at least one target histological image to the histological image, according to one embodiment of the present disclosure.

FIG. 2 is a flow diagram for identifying at least one target histological image corresponding to a target region in a histological image 210 captured by the medical imaging device 100 and generating a modified image 120 of the histological image 210, according to one embodiment of the present disclosure. The medical imaging device 100 may capture or generate a histological image 210 (e.g., a 2-dimensional histological image) of a body portion of the patient 30 and provide it to the image processing device. For example, as shown in FIG. 2, the histological image 210 may include at least one type of tissue in a breast of the patient 30.

In one embodiment, the image processing device may be configured to input the histological image 210 to a first autoencoder so as to determine a candidate type of tissue in the histological image 210 and identify a target region corresponding to the candidate type of tissue in the histological image 210. The first autoencoder may be any type of artificial neural network used for unsupervised learning of efficient codings. In addition, the first autoencoder may be trained for generating a first unsupervised learning model, as will be described in detail later with reference to FIG. 4. The candidate type of tissue may include any meaningful or suspicious locations in the histological image 210. For example, the candidate type of tissue may be cell nuclei, tumors, or the like.

Upon identifying the target region in the histological image 210, the image processing device may identify at least one target histological image corresponding to the target region in the histological image based on a predictive model associating one or more histological images with one or more target histological images. In one embodiment, a target histological image may be any histological image that may be modified from a histological image captured by the medical imaging device 100 for improving visibility or discernibility of the captured histological image. The at least one target histological image may be used to modify the captured image based on its display characteristics. For example, if a histological image is captured by an OCT device, at least one target histological image may be one or more images of H&E stain. According to one embodiment, the predictive model may be generated as an extension of the first unsupervised learning model, and may be any type of artificial neural network for semi-supervised learning of efficient codings. For example, using both an unsupervised machine learning technique and a supervised machine learning technique, which may be referred as a semi-supervised machine learning technique, may be applied to generate the predictive model, as will be described in detail later with reference to FIG. 6.

Upon identifying the at least one target histological image corresponding to the target region in the histological image 210, the image processing device may apply one or more display characteristics associated with the at least one target histological image to the histological image 210. For example, one or more display characteristics may include one or more features such as colors, shapes, and/or sharpness of points or patches, arrangement, distribution and/or density of points or patches with similar characteristics in a histological image and a target histological image. A patch may be an area or region in a histological image that can be a unit or window for processing the image (e.g., 8×8 pixels). The target histological image may be segmented on a basis of such unit or window. According to one embodiment, the image processing device may change one or more display characteristics of the histological image 210 based on one or more display characteristics of the identified histological image. In this process, any suitable style transfer techniques may be adopted to change the histological image 210 in a style of the identified target histological image. For example, if the histological image, e.g., the image 210, is captured by an OCT device, it may be modified to appear in a form of H&E stain, e.g., the image 120 as shown in FIG. 2.

According to one embodiment, the image processing device may generate the modified image 120 including the one or more display characteristics associated with the identified target histological image. For example, the image processing device may change values of color components (e.g., red (R), green (G), Blue (B) values) and a value of sharpness of each pixel in the target region. As shown in the image 120 modified from the histological image 210, shades of red (e.g., a scarlet) color may be assigned to the target region and a portion around the center of the target region is adjusted to improve visibility of the target region. Thus, the modified image 120 with high quality of visibility can allow the doctors 10 and/or 20 to diagnose the patient 30 more accurately than using the histological image 210 originally captured by the device 100. In some embodiments, the image processing device may process the histological image 210 to generate the modified image 120 such that the doctors 10 and/or 20 may be provided with the modified image 120 readily, even during the surgery. Similarly, a 3-dimensional histological image captured by the medical imaging device 100 may be provided to the image processing device and modified in a style of a target histological image. In this case, a modified image of the 3-dimensional histological image may be displayed on the display device 110. In addition, if the doctors 10 and/or 20 may select a portion of the 3-dimensional histological image, a modified image of a 2-dimensional histological image corresponding to the selected portion may be displayed on the display device 110.

Figure 3:
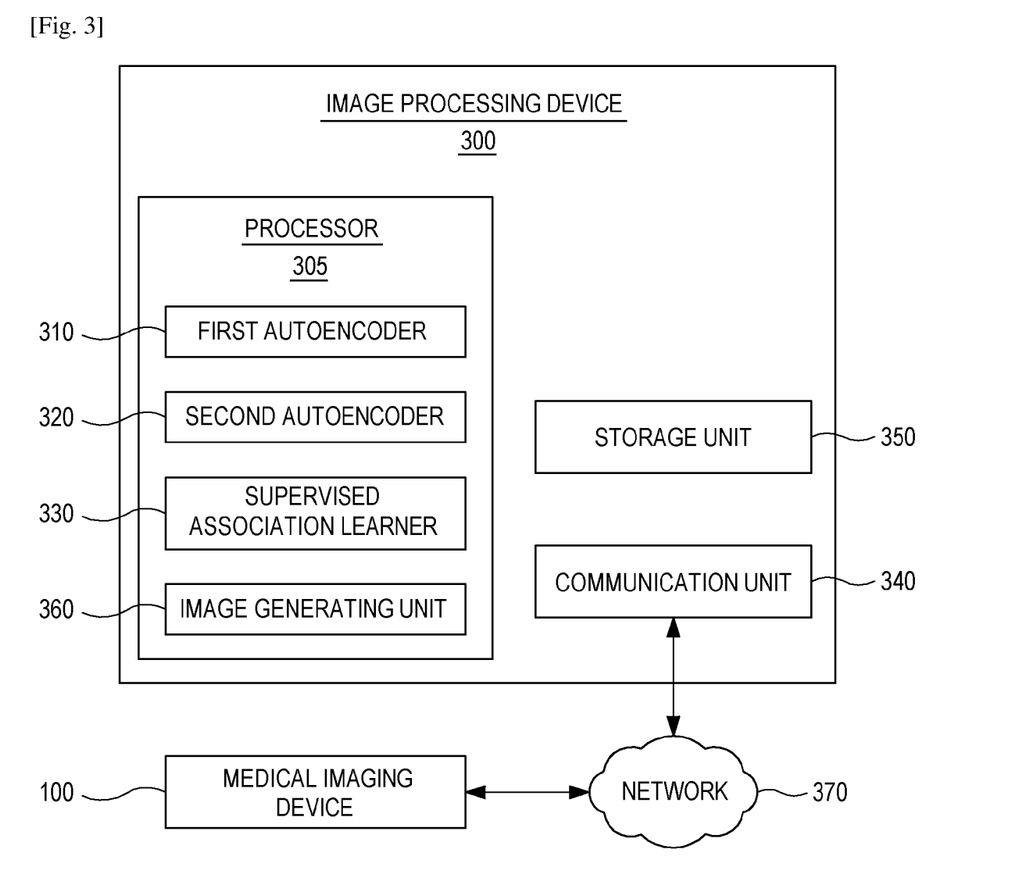
FIG. 3 illustrates a block diagram of an image processing device configured to generate a predictive model by training a first autoencoder, a second autoencoder, and a supervised association learner and process a histological image based on the first autoencoder and the predictive model, according to one embodiment of the present disclosure.

FIG. 3 illustrates a block diagram of an image processing device 300 configured to generate a predictive model by training a first autoencoder 310, a second autoencoder 320, and a supervised association learner 330 and process a histological image based on the first autoencoder 310 and the predictive model, according to one embodiment of the present disclosure. The image processing device 300 may include a processor 305, a communication unit 340, and/or a storage unit 350. The processor 305 in the image processing device 300 may include the first autoencoder 310, the second autoencoder 320, the supervised association learner 330, and/or an image generating unit 360.

The image processing device 300 is configured to communicate with the medical imaging device 100 through the communication unit 340 via a communication network 370. In some embodiments, the image processing device 300 may communicate with the medical imaging device 100 through any type of wired/wireless connection including, but not limited to, an electrical data cable and a short-range wireless network such as Bluetooth, ZigBee, infrared transmission, etc. Even though the image processing device 300 is shown in FIG. 3 to be a separate device from the medical imaging device 100, in some embodiments, the medical imaging device 100 and the image processing device 300 may be integrated in a single device.

The first autoencoder 310 in the processor 305 may be configured to receive a plurality of histological images and a plurality of sample histological images from the storage unit 350. Also, the first autoencoder 310 may be trained based on the received histological images and the plurality of sample histological images, thereby generating a first unsupervised learning model. Any suitable unsupervised learning technique including, but not limited to, K-means clustering, etc. may be utilized to train the first autoencoder 310. Similarly, the second autoencoder 320 in the processor 305 may be configured to receive a plurality of target histological images and a plurality of sample target histological images from the storage unit 350 and be trained based on the received target histological images and the plurality of sample target histological images to generate a second unsupervised learning model. The first autoencoder 310 may include an artificial neural network used for unsupervised learning of efficient coding of the histological images while the second autoencoder 320 may include an artificial neural network used for unsupervised learning of efficient coding of the target histological images. In some embodiments, the first autoencoder 310 and the second autoencoder 320 may include multi-layer autoencoders, including stacked autoencoders, multi-layer convolutional autoencoders, etc. Although autoencoders are illustrated as an example of unsupervised learning unit or method, any other suitable type of unsupervised machine learning method including, but not limited to, generative adversarial networks (GANs), self-organizing map (SOM), adaptive resonance theory (ART), k-means clustering, and/or expectation-maximization algorithm (EM) may be used for such a unit. Further, even though the histological images, the sample histological images, the target histological images, and/or the sample target histological images are illustrated as being stored in the storage unit 350, at least some of the images may be stored in one or more external storage units.

The processor 305 may be configured to train the first autoencoder 310 based on a plurality of sample histological images for generating a first unsupervised learning model. The first unsupervised learning model may be stored in the storage unit 350 or may be incorporated into the first autoencoder 310. In one embodiment, the first autoencoder 310 may be trained to perform a semantic segmentation (e.g., identify a target region) in each of the sample histological images. During the semantic segmentation, the first autoencoder 310 may be trained to determine a candidate type of tissue in each of the sample histological images and identify a target region corresponding to the candidate type of tissue in the sample histological image. In this process, the first autoencoder 310 may be configured to extract features from the sample histological image and classify the sample histological image into a group with features, which are similar to the features from the sample histological image. For example, the first autoencoder 310 may determine a similarity (e.g., a distance or probability) between the features from the sample histological image and each of features or parameters (e.g., a hidden layer of an artificial neural network) in the first unsupervised learning model and select a set of features or parameters with the greatest similarity (e.g., a smallest distance) to the sample histological image from the features or parameters in the first unsupervised learning model. In this case, the features or parameters in the first unsupervised learning model may be generated based on features extracted in one or more sample histological images, and be represented as model hyperparameters such as the topology of the network (e.g., number and width of layers, filter sizes, etc.), activation functions, etc. and the learned weights and biases of that network.

Upon selecting the set of features or parameters with the greatest similarity to the sample histological image, the sample histological image may be determined to correspond to the selected set of features or parameters in the first unsupervised learning model. The first autoencoder 310 may then determine a candidate type of tissue in the sample histological image and identify a target region corresponding to the candidate type of tissue based on the selected set of features or parameters in the first unsupervised learning model. In this process, the first autoencoder 310 may identify a plurality of regions including the target region in the sample histological image based on the selected set of features or parameters. For example, the plurality of regions may correspond to a plurality of regions associated with the selected features or parameters in the first unsupervised learning model. In this case, the plurality of regions may be indicative of one or more tissue cells, air, etc.

The processor 305 may train the first autoencoder 310 to generate the first unsupervised learning model by performing the semantic segmentation in each of sample histological images. In one embodiment, the first autoencoder 310 may classify the sample histological image into a group with selected set of features or parameters corresponding to the features of the sample histological image. In this process, the parameters associated with the group are updated or adjusted based on the extracted features for the identified target region or the identified plurality of regions in the histological image. The identified plurality of regions including the target region, which corresponds to the candidate type of tissue in the histological image may be identified and provided to the image generating unit 360 for generating a modified image of the histological image. In some embodiment, the first autoencoder 310 may receive a histological image captured by the medical imaging device 100 and be trained to perform a semantic segmentation in the histological image in the similar manner to the sample histological images.

The second autoencoder 320 may be trained based on the received target histological images and the sample target histological images for generating a second unsupervised learning model. The second unsupervised learning model may be stored in the storage unit 350 or may be incorporated into the second autoencoder 320. According to one embodiment, the second autoencoder 320 may be trained in a similar manner to the first autoencoder 310 for generating the second unsupervised learning model. In this process, the second autoencoder 320 may extract one or more features from each of the received target histological images and the sample target histological images. Then, the second unsupervised learning model may group the target histological images and the sample target histological images in the similar manner to those of the first unsupervised learning model based on the extracted features to generate the second unsupervised learning model. The generated second supervised learning model may be accessed by the supervised association learner 330 in the processor 305.

The supervised association learner 330 may be configured to generate a predictive model by associating the second unsupervised learning model with the first unsupervised learning model based on a golden set of matching images, according to one embodiment of the present disclosure, as will be described in detail with reference to FIG. 6. The golden set of matching images may indicate any set of images, which may include one or more sample histological images and one or more sample target histological images that correspond to the sample histological images. In the golden set of matching image, each of the sample histological images may include the same tissue or anatomical locations in a human body as that of each of the sample target histological images. For example, the supervised association learner 330 may associate a plurality of regions in a histological image including a target region corresponding to a particular type of tissue in the first unsupervised learning model with features indicative of one or more display characteristics of a plurality of regions in a sample target histological image corresponding to the histological image. In one embodiment, the predictive model may be represented as a deep-learning neural network based structure that may be defined by parameters such as model hyperparameters such as the topology of the network (e.g., number and width of layers, filter sizes, etc.), activation functions, etc. and the learned weights and biases of that network. For example, the parameters of the predictive model may represent mapping or transfer functions for associating a plurality of display characteristics with, for example, the target histological images, the sample target histological images, the histological images, and the sample histological images.

The storage unit 350 in the image processing device 300 is configured to store a first database of sample histological images captured by the medical imaging device 100 and/or a second database of sample target histological images including at least one image of at least one predetermined tissue stain. For example, the second database may include sample histological images of H&E stain. In one embodiment, the storage unit 350 may include the first unsupervised learning model generated by the first autoencoder 310 and the second unsupervised learning model generated by the second autoencoder 320. Although the storage unit 350 is illustrated as being part of the image processing device 300 in this embodiment, it may be at least partially included in an external device that can be configured to communicate with the image processing device 300. The storage unit 350 may be implemented using any suitable storage or memory device such as a ROM (Read Only Memory), a RAM (Random Access Memory), a flash memory, an EEPROM (Electrically Erasable Programmable Read Only Memory), etc.

The storage unit 350 may also store a golden set of matching images that include a predetermined number (e.g., positive integer M) of sample histological images in the first database of sample histological images and a predetermined number (e.g., positive integer N) of sample target histological images in the second database of sample target histological images. One or more features (e.g., anatomical locations) of the M number of the sample histological images in the first database may be associated or aligned to match one or more features (e.g., anatomical locations) of the N number of sample target histological images in the second database. For example, voxels or pixels in each of the M number of sample histological images have the same locations as those in each of the N number of sample histological images.

The image generating unit 360 in the image processing device 300 is configured to receive the target region for the histological image from the first autoencoder 310 and modify the histological image for improving visibility of the target region. According to one embodiment, the image generating unit 360 may identify at least one target histological image corresponding to the target region in the histological image based on the predictive model. The image generating unit 360 may then apply one or more display characteristics associated with the at least one target histological image to the histological image. According to one embodiment, one or more display characteristics for each of a plurality of regions in the at least one target histological image may be applied to each of corresponding regions in the histological image. In this case, the display characteristics may be indicative of an image style associated with the at least one target histological image, and for example, include one or more features or parameters such as colors, shapes, and/or sharpness of points or patches, arrangement, distribution and/or density of points or patches with similar characteristics in at least one target histological image. By applying the display characteristics for the at least one target histological image to the histological image, an image style of the histological image may be transferred to an image style of the at least one target histological image. A modified image of the histological image including the applied display characteristics may be generated and provided to a display unit for displaying the modified image to a user such as a doctor.

Figure 4:
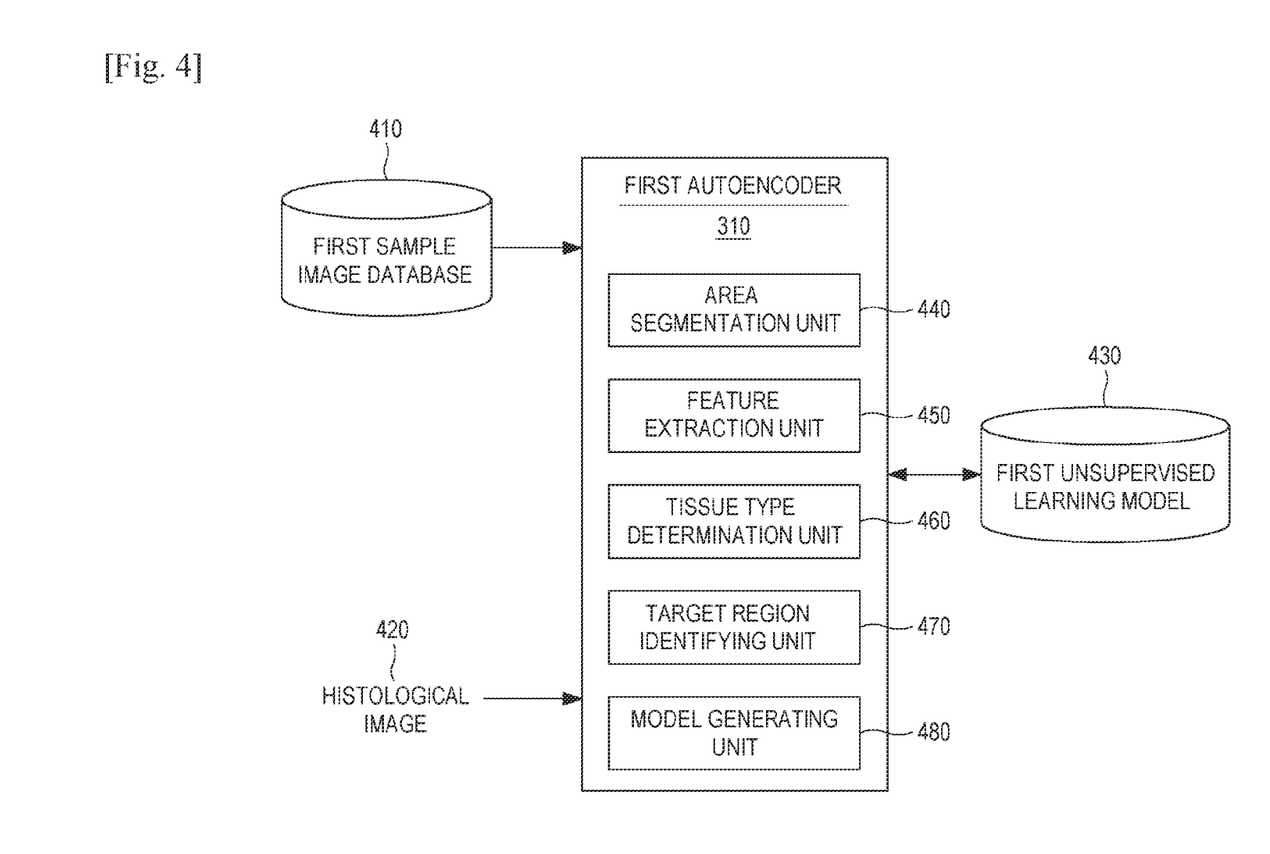
FIG. 4 depicts a block diagram of a first unsupervised learning model that may be generated by training a first autoencoder based on sample histological images in a first sample image database of histological images, according to one embodiment of the present disclosure.

FIG. 4 depicts a block diagram of the first autoencoder 310 configured to be trained to generate a first unsupervised learning model 430 based on sample histological images in a first sample image database 410 and a histological image 420, according to one embodiment of the present disclosure. The first autoencoder 310 may include an area segmentation unit 440, a feature extraction unit 450, a tissue type determination unit 460, a target region identifying unit 470, and a model generating unit 480. The first sample image database 410 may include sample histological images captured by the medical imaging device 100 (e.g., OCT device). Even though the histological image 420 is illustrated as being input to the first autoencoder 310, it will be appreciated that a plurality of histological images may be input to the first autoencoder 310 for training the first autoencoder 310.

The area segmentation unit 440 in the first autoencoder 310 is configured to receive 3-dimensional or 2-dimensional sample histological images from the first sample image database 410 and segment one or more areas in each of the sample histological images. In one embodiment, the area segmentation unit 440 may segment a plurality of patches in the sample histological image. According to other embodiments, the one or more areas in the sample histological image may be segmented by determining one or more blobs with one or more similar properties such as brightness, locations of points, etc. Upon determining the blobs in the sample histological image, the area segmentation unit 440 may cluster the blobs in a patch clustering operation. For example, a plurality of blobs having brightness values within a predetermined range of brightness values and located in proximity may be clustered in a blob cluster. The segmented areas may be provided to the feature extraction unit 450 in the first autoencoder 310.

The feature extraction unit 450 is configured to extract one or more features from the segmented areas in the sample histological image from the area segmentation unit 440. In one embodiment, the feature extraction unit 450 may extract the features characterizing the areas such as pattern, density of points, distribution or space of points, etc. For example, the features may be extracted from the areas by using any suitable feature extraction techniques such as a scale-invariant feature transform technique, a template matching technique, or the like. In this case, the features may be represented as a feature vector, which may include a set of numbers. The features as extracted may be provided to the tissue type determination unit 460 in the first autoencoder 310.

The tissue type determination unit 460 is configured to receive one or more features for the sample histological image from the feature extraction unit 450 and determine at least one candidate type of tissue in the sample histological image. In this process, the tissue type determination unit 460 may select a set of one or more features or parameters in the first unsupervised learning model 430 that are similar to the features for the sample histological image. The at least one candidate type of tissue in the sample histological image may be determined based on the selected set of parameters or features. For example, types of tissue may include any type of tissue, which may characterize any normal cells or abnormal cells such as a tumor, a cancer, etc. The determined candidate types of tissue and the selected set of parameters or features may be provided to the target region identifying unit 470 in the first autoencoder 310.

The target region identifying unit 470 is configured to receive the candidate types of tissue in the sample histological image and/or the parameters or features of the selected group from the tissue type determination unit 460 and identify a target region corresponding to the candidate type of tissue from the regions in the sample histological image based on the selected set of parameters or features. According to one embodiment, the target region in the sample histological image may be identified by detecting the target region that corresponds to a region having the determined candidate types of tissue that are defined by the selected set of parameters or features of the first unsupervised learning model 430. In addition, the target region identifying unit 470 may identify a plurality of regions including the target region in the sample histological image based on the selected set of parameters or features in the first unsupervised learning model 430. In this case, the selected set of parameters or features may be indicative of the target region and one or more peripheral regions in the sample histological image. The features for the identified regions including the target region in the sample histological image may be provided to the model generating unit 480.

The model generating unit 480 may be configured to receive the features for the identified regions in the sample histological image and generate, train, and/or adjust the first unsupervised learning model 430 by training the first autoencoder 310. According to one embodiment, the model generating unit 480 may update or adjust the selected set of parameters or features for the sample histological image based on the features for the identified regions including the target region in the sample histological image. If a set of parameters or features is not selected for the sample histological image, the features extracted from the sample histological image may be used to define a newly classified group in the first unsupervised learning model 430. Even though a plurality of sample histological images are illustrated as being used for training the first autoencoder 310 in this embodiment, a plurality of histological images captured by the medical imaging device 100 may be used for training the first autoencoder 310 in the similar manner to the sample histological images. Even though the first autoencoder 310 is illustrated as being the separate units 440, 450, 460, 470, and 480, the first autoencoder 310 may be implemented as a single unit or any combination of the separate units 440, 450, 460, 470, and/or 480. In addition, although the sample histological images are illustrated as being used for performing a semantic segmentation and training the first autoencoder 310, the histological image 420 may be used for performing a semantic segmentation and/or training the first autoencoder 310 in the similar manner to the sample histological images. The generated or updated first unsupervised learning model 430 may be used for generating the predictive model 620, as will be described with reference to FIG. 6.

Figure 5:
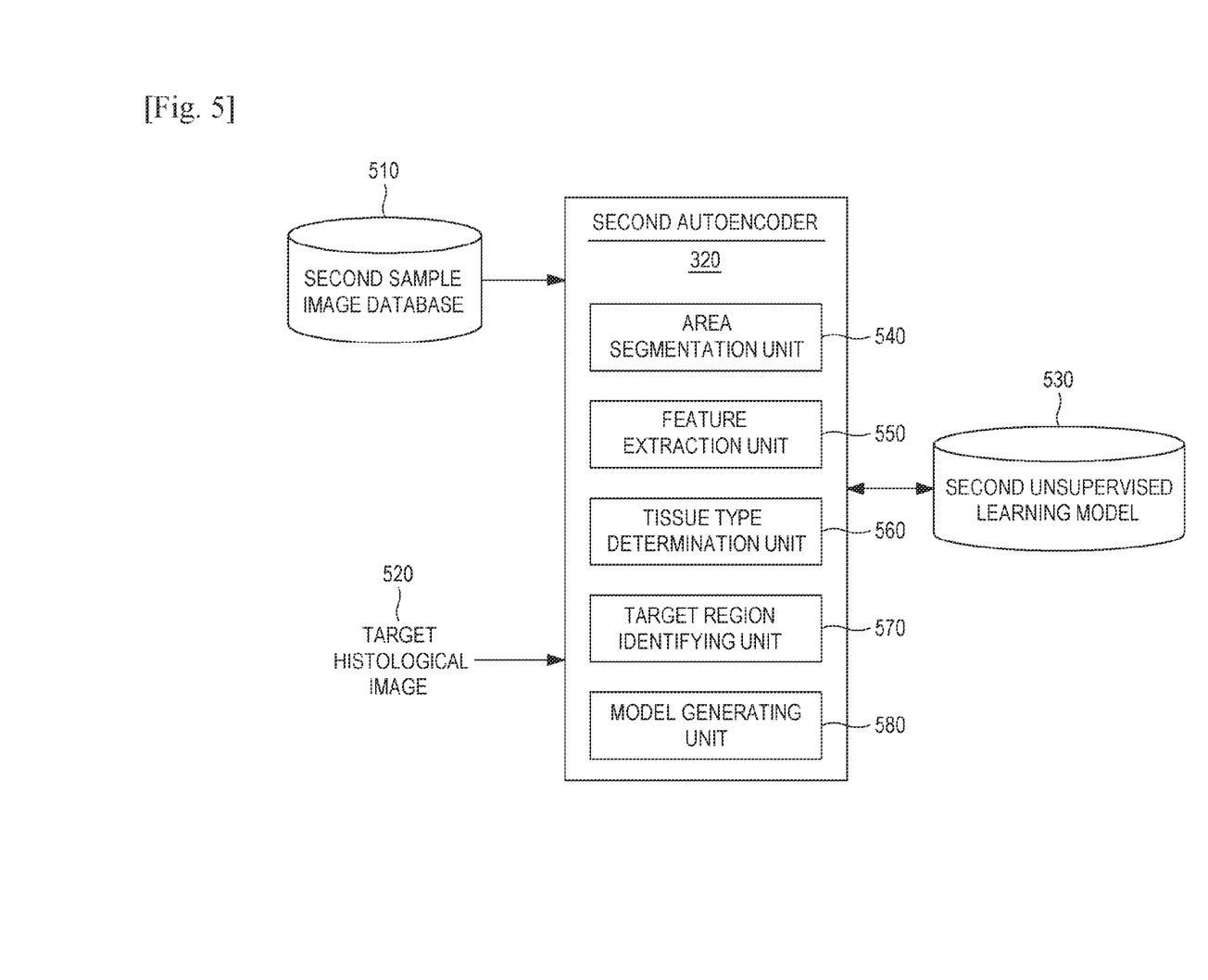
FIG. 5 illustrates a block diagram of a second unsupervised learning model that may be generated by training a second autoencoder based on sample target histological images in a second sample image database of target histological images, according to one embodiment of the present disclosure.

FIG. 5 illustrates a block diagram of a second autoencoder 320 configured to be trained to generate a second unsupervised learning model 530 based on sample histological images in a second sample image database 510 and input target histological images 520, according to one embodiment of the present disclosure. The second autoencoder 320 may include an area segmentation unit 540, a feature extraction unit 550, a tissue type determination unit 560, a target region identifying unit 570, and a model generating unit 580. According to one embodiment, the second sample image database 510 may include sample target histological images including at least one image of at least one predetermined tissue stain (e.g., images of H&E stain). Even though the target histological image 520 is illustrated as being input to the second autoencoder 320, it will be appreciated that a plurality of target histological images may be input to the second autoencoder 320 for training the second autoencoder 320.

The second autoencoder 320 may be configured to perform a semantic segmentation on the sample target histological images and the target histological images and generate, train, and/or update the second unsupervised learning model 530. To this end, the area segmentation unit 540, the feature extraction unit 550, the tissue type determination unit 560, the target region identifying unit 570, and the model generating unit 580 in the second autoencoder 320 may serve similar functions or operations to the area segmentation unit 440, the feature extraction unit 450, the tissue type determination unit 460, the target region identifying unit 470, and the model generating unit 480, respectively. The generated or updated second unsupervised learning model 530 may be used for generating the predictive model 620, as will be described with reference to FIG. 6.

Figure 6:
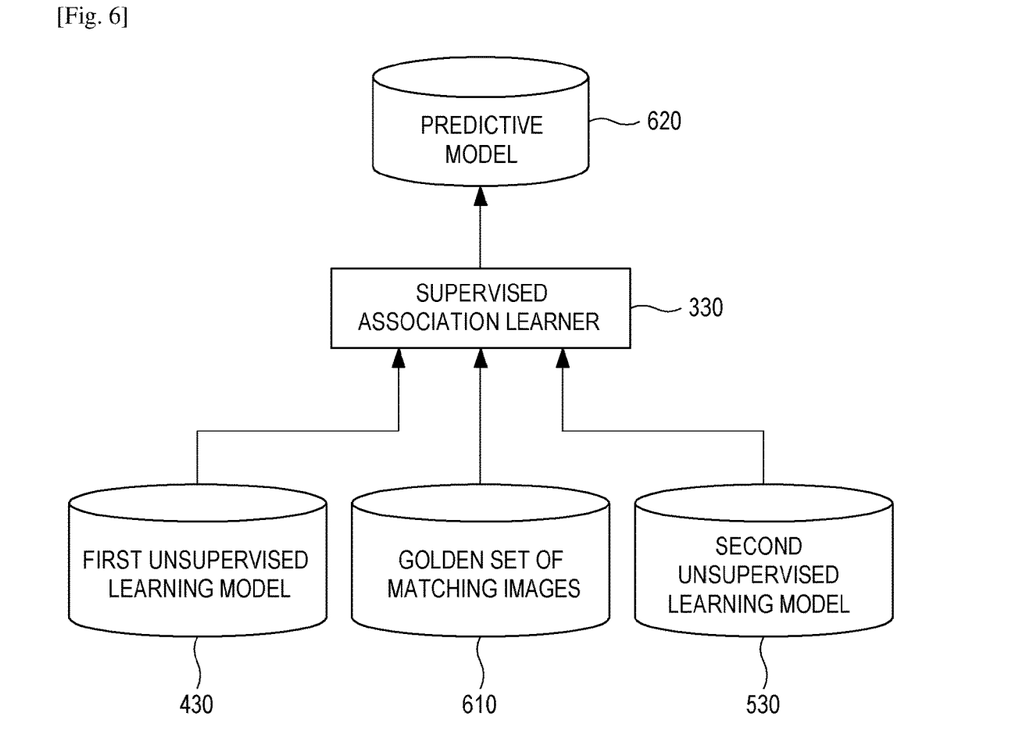
FIG. 6 shows the supervised association learner in the image processing device that is configured to generate the predictive model by associating the second unsupervised learning model with the first unsupervised learning model based on a golden set of matching images, according to one embodiment of the present disclosure.

FIG. 6 shows the supervised association learner 330 in the image processing device 300 that is configured to generate a predictive model 620 by associating the second unsupervised learning model 530 with the first unsupervised learning model 430 based on a golden set of matching images 610, according to one embodiment of the present disclosure. In one embodiment, the predictive model may represent a deep-learning neural network based structure. The predictive model may include a plurality of parameters that may be defined by the model hyperparameters such as the topology of the network (e.g., number and width of layers, filter sizes, etc.), activation functions, etc. and the learned weights and biases of that network. The parameters in the predictive model 620 may include one or more features indicative of one or more display characteristics for each of the histological images and the target histological images.

Figure 7:
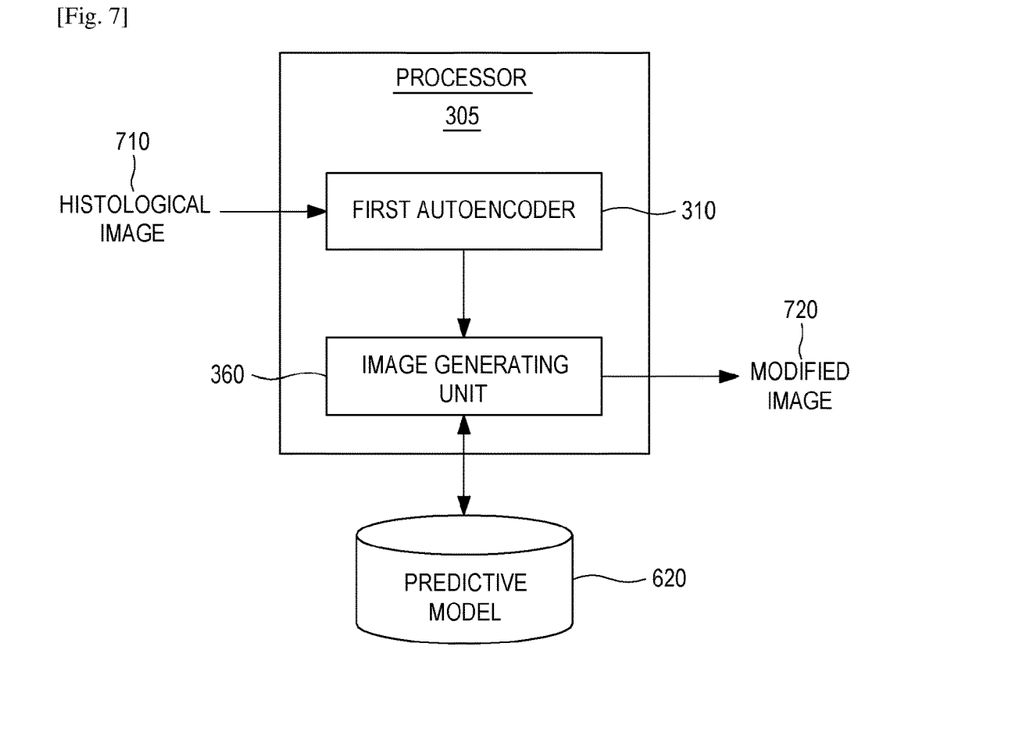
FIG. 7 depicts a block diagram of an image generating unit and a first autoencoder in a processor that are used for generating a modified image of a histological image based on a predictive model, according to one embodiment of the present disclosure.

In one embodiment, the predictive model 620 may include a first set of patches in each of the histological images and a second set of patches in each of the target histological images, wherein the first set of patches is associated with the second set of patches in the predictive model. The image generating unit 360 may apply the one or more display characteristics associated with the at least one target histological image and/or generate the modified image 720 by modifying a plurality of patches in the received histological image based on the second set of patches in the identified at least one target histological image.

The golden set of matching images 610 may include one or more sample histological images in the first sample image database 410 and one or more sample target histological images in the second sample image database 510, where the sample histological images are aligned to match anatomical locations of the sample target histological images. According to one embodiment, a sample histological image may have the same anatomical location as that of each of one or more sample target histological images. Similarly, a sample target histological image may have the same anatomical location as that of each of one or more sample histological images.

The supervised association learner 330 is configured to associate at least one feature indicative of one or more display characteristics that are extracted from a sample target histological image in the golden set of matching images 610 with one or more sample histological images in the golden set of matching images 610. In this process, at least one feature from the sample target histological images may be correlated to a plurality of regions in each of the sample histological images that may be included in the second unsupervised learning model 530. As such, existing or known display characteristics corresponding to the at least one feature from the sample target histological image (e.g., image of H&E stain) in the second unsupervised learning model 530 may be transferred to the features from the plurality of regions in each of the sample histological images (e.g., M2™ images) in the first unsupervised learning model 430. The predictive model 620 may then be generated or trained by associating the at least one feature from the sample target histological image (i.e., image of H&E stain) with the sample histological image (e.g., M2™ images). For example, the predictive model may be trained to generate a similarity metric for the first and second unsupervised learning models.

The supervised association learner 330 is configured to use one or more labels for each of one or more sample target histological images in the golden set of matching images 610 to train and/or update the predictive model 620. The labels may indicate any data or information (e.g., cell nuclei, tumor, etc.) identifying one or more regions in the sample target histological image. The labels for the regions in the sample target histological image may be determined based on data or information for the sample target histological image that may be input by an experimenter or a user. The supervised association learner 330 may assign the labels for the sample target histological image of the second sample image database 510 to a corresponding sample histological image for training the predictive model 620.

In one embodiment, each of the first unsupervised learning model 430, the second unsupervised learning model 530, and the predictive model 620 may include a multilayer model defined by one or more model hyperparameters and/or one or more weights of an artificial neural network.

FIG. 7 depicts a block diagram of the image generating unit 360 and the first autoencoder 310 in the processor 305 that are used for generating a modified image 720 of a histological image 710 based on a predictive model 620, according to one embodiment of the present disclosure. The processor 305 may receive the histological image 710 that may be captured by any medical imaging device (e.g., the medical imaging device 100), and generate the modified image 720 of the histological image 710 for improving visibility of the histological image 710. In this process, the processor 305 may access the predictive model 620 to modify the histological image 710.

The first autoencoder 310 in the processor 305 may perform a semantic segmentation on the received histological image. According to one embodiment, the first autoencoder 310 may perform segmentation in the histological image and extract one or more features from the histological image. Based on the features, the first autoencoder 310 may classify the histological image into a group with features or parameters that are similar to the extracted features. Based on the features or parameters of the group, a candidate type of tissue in the histological image may be determined and a target region corresponding to the candidate type of tissue may be identified. In this process, a plurality of regions including the target region may be identified by comparing the extracted features to the selected features or parameters of the group. The identified regions including the target region may then be provided to the image generating unit 360 in the processor 305.

The image generating unit 360 may be configured to receive the identified regions in the histological image and generate a modified image 720 based on the predictive model 620. According to one embodiment, the image generating unit 360 may be configured to identify features indicative of one or more display characteristics for at least one target histological image that correspond to the features for the target region in the predictive model 620. For example, the image generating unit 360 may detect features of a group for one or more histological images that are similar to the features of the identified regions and identify features of a group for at least one target histological image that are correlated to the group for the histological images. One or more display characteristics associated with the features of the group for the at least one target histological image may be applied to each of the identified regions of the histological image 710. For example, one or more display characteristics are associated with a plurality of features such as colors, shape, arrangement, distribution, density, sharpness of patches (e.g., n×n pixels where n is a positive integer), etc. in the group for at least one target histological image. According to one embodiment, the image processing device may change one or more display characteristics of the histological image 710 based on the one or more display characteristics of the group for at least one target histological image. In this process, any suitable style transfer techniques may be adopted to change the histological image 710 in a style of the group for the at least one target histological image. According to one embodiment, the image generating unit 360 may generate the modified image 720 by modifying the identified regions of the histological image 710 in the histological image 710 based on the features associated with the group of the at least one target histological image. The modified image 720 may then be displayed on a display unit (e.g., display device 110) for diagnosing a disease or illness that may be identified from the modified image 720.

In one embodiment, the image generating unit 360 may generate the modified image 720 of the histological image 710 using one or more known generative networks such as cycle-consistent adversarial networks, which may be implemented by a Cycle GAN technique. In this case, the predictive model 620 may be trained by the cycle-consistent adversarial networks. In this process, a first mapping function G and a first adversarial discriminator $D_x$ may be used to translate and/or modify one or more sample histological images based on one or more sample target histological images while a second mapping function F and a second adversarial discriminator $D_y$ may be used to translate and/or modify the sample target histological images based on the sample histological images. To regulate such mappings, a first cycle consistency loss may be determined when the sample histological images are translated to the sample target histological images using the first mapping function and the first adversarial discriminator. Similarly, a second cycle consistency loss may be determined when the sample target histological images are translated to the sample histological images using the second mapping function and the second adversarial discriminator. The predictive model for the sample histological images and the sample target histological images may be generated based on the first and second mapping functions, the first and second adverbial discriminators, and/or the first and second cycle consistency losses. Based on the predictive model generated by the Cycle GAN technique, the histological image 710 (e.g., M2™ image) may be modified to the image 720 (e.g., image of H&E stain).

Figure 8:
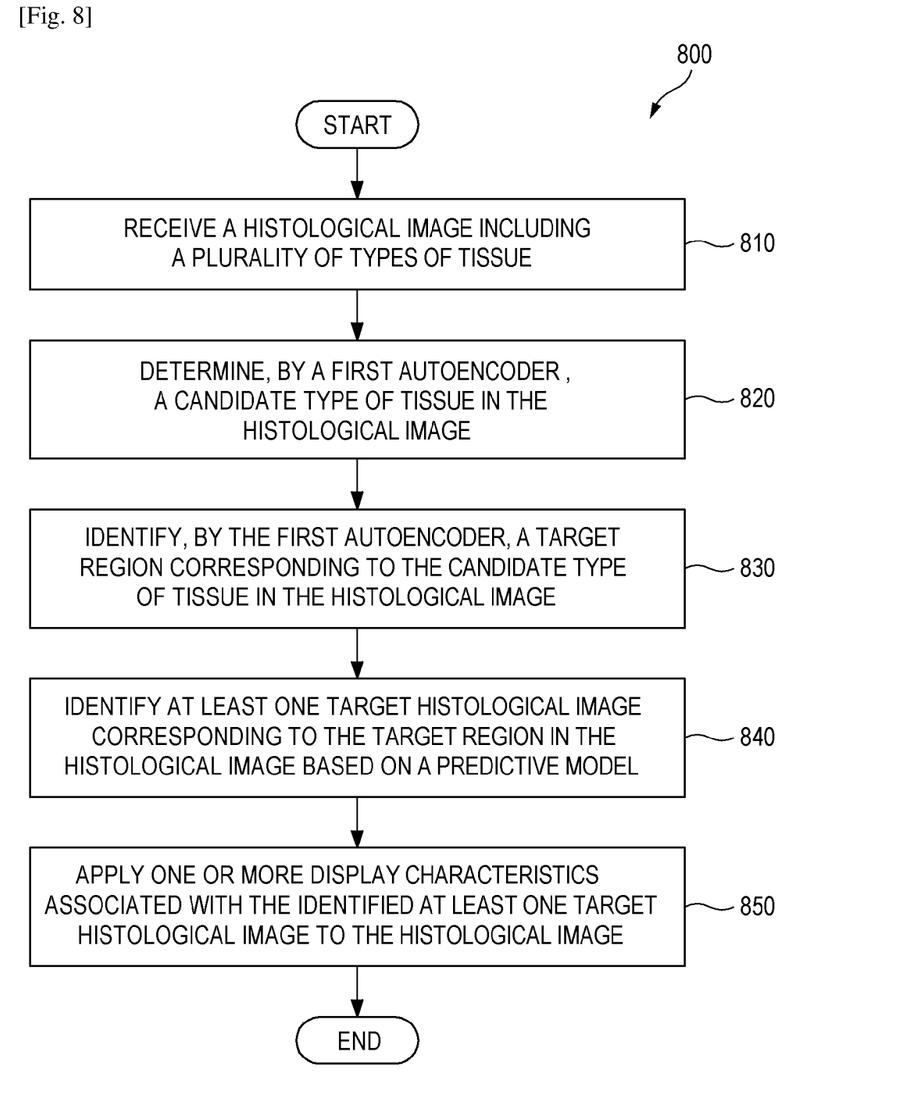
FIG. 8 is a flow chart of a method for receiving a histological image captured by a medical imaging device and generating a modified image of the histological image by using a first autoencoder and a predictive model, according to one embodiment of the present disclosure.

FIG. 8 depicts a flow chart of a method 800 for receiving a histological image captured by a medical imaging device and generating a modified image of the histological image by, for example, using a first autoencoder (e.g., first autoencoder 310) and a predictive model (e.g., predictive model 620), according to one embodiment of the present disclosure. The method 800 may be performed by a computer, a processor, a medical device, an image processing device, or a module that is part of the medical device. In one embodiment, a non-transitory computer-readable storage medium may include instructions for processing one or more histological images, the instructions causing a processor of a computer to perform the method 800. Initially, an image processing device (e.g., image processing device 300) may receive a histological image including at least one type of tissue, at 810. At 820, the first autoencoder in the image processing device may determine a candidate type of tissue in the received histological image. At 830, the first autoencoder may identify a target region corresponding to the candidate type of tissue in the histological image.

At 840, a model generating unit (e.g., model generating unit 480) may identify at least one target histological image corresponding to the target region in the histological image based on a predictive model. The predictive model may be generated based on any suitable combination of an unsupervised deep learning technique and a supervised deep learning technique. At 850, an image generating unit (e.g., image generating unit 360) may apply one or more display characteristics associated with the identified at least one target histological image to the histological image to modify the histological image. The modified image may result in improving visibility of the target region.

Figure 9:
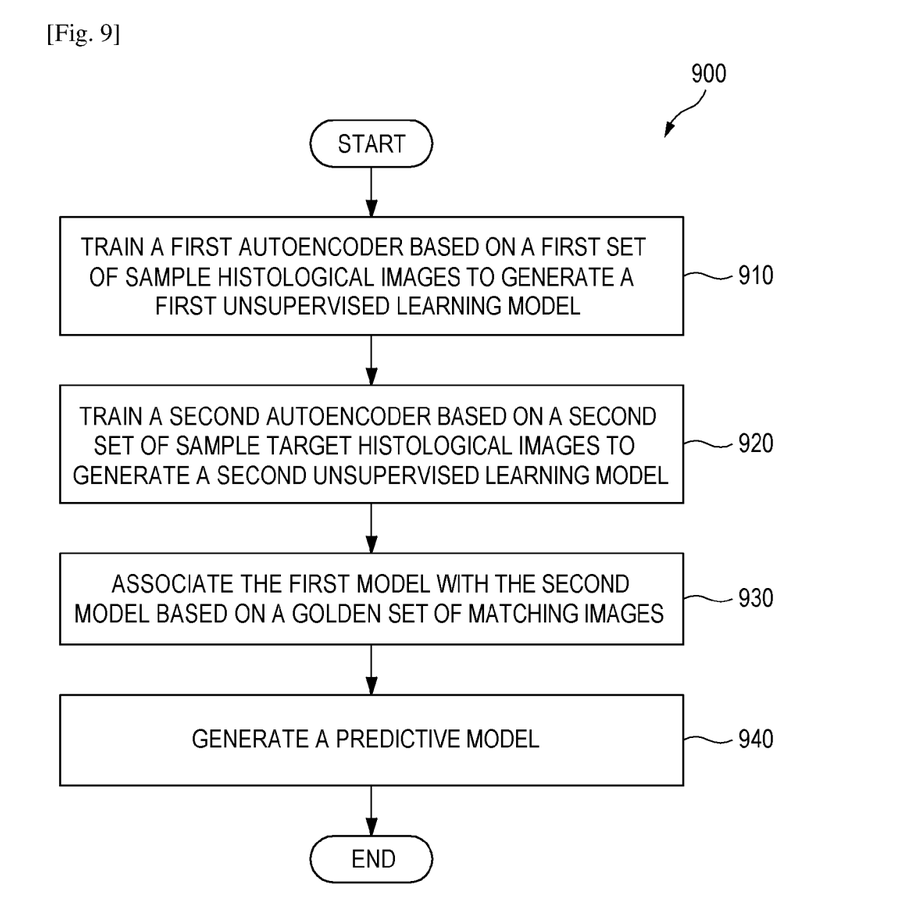
FIG. 9 is a flow chart of a method for generating a predictive model by training first and second autoencoders to generate first and second unsupervised learning models and associating the second unsupervised learning model with the first unsupervised learning model based on a golden set of matching images, according to one embodiment of the present disclosure.

FIG. 9 is a flow chart of a method 900 for generating a predictive model (e.g., predictive model 620) by training first and second autoencoders (e.g., first and second autoencoders 310 and 320) to generate first and second unsupervised learning models and associating the second unsupervised learning model with the first unsupervised learning model based on a golden set of matching images, according to one embodiment of the present disclosure. The method 900 may be performed by a computer, a processor, a medical device, an image processing device, or a module that is part of the medical device. In one embodiment, a non-transitory computer-readable storage medium may include instructions for processing one or more histological images, the instructions causing a processor of a computer to perform the method 900. Initially, a processor (e.g., processor 305) may train a first autoencoder (e.g., first autoencoder 310) based on a first set of sample histological images to generate the first unsupervised learning model, at 910. At 920, the processor may train a second autoencoder (e.g., second autoencoder 320) based on a second set of sample target histological images to generate the second unsupervised learning model. A supervised association learner (e.g., supervised association learner 330) may associate the first unsupervised learning model with the second unsupervised learning model based on a golden set of the matching images, at 930. At 940, the predictive model 620 may be generated and/or trained and used for processing an input histological image captured by a medical imaging device (e.g., medical imaging device 100).

It will be apparent to those skilled in the art that various modifications and variation can be made in the present disclosure without departing from the spirit or scope of the present disclosure. Thus, it is intended that the present disclosure cover the modifications and variations of the present disclosure provided they come within the scope of the appended claims and their equivalents.

The invention claimed is:

1. A method, performed by an image processing device comprising a processor, a storage, and a communication unit, for processing a histological image captured by a medical imaging device, the method comprising:
receiving the histological image including at least one type of tissue;
determining, by a first autoencoder of the processor, a candidate type of tissue in the histological image;
identifying, by the first autoencoder of the processor, a target region corresponding to the candidate type of tissue in the histological image;
identifying at least one target histological image corresponding to the target region in the histological image based on a predictive model associating one or more sample histological images with one or more sample target histological images;
applying one or more display characteristics associated with the identified at least one target histological image to the histological image; and
generating a modified image of the histological image including the applied one or more display characteristics,
wherein a first unsupervised learning model is generated by training the first autoencoder of the processor based on a first set of sample histological images, and a second unsupervised learning model is generated by training a second autoencoder of the processor based on a second set of sample target histological images,
wherein the predictive model is generated by associating the second unsupervised learning model with the first unsupervised learning model based on a set of matching images,
wherein the set of matching images include M sample histological images in the first set of sample histological images and N sample target histological images in the second set of sample target histological images,
wherein one or more anatomical locations of the M sample histological images in the first set of sample histological images are aligned to match one or more anatomical locations of the N sample target histological images in the second set of sample target histological images, M and N being positive integers,
wherein the predictive model comprises data regarding one or more features indicative of at least one display characteristic and is trained by associating one or more features from the N sample target histological images with one or more features from the M sample histological images,
wherein the predictive model comprises a first set of patches in each of the one or more sample histological images and a second set of patches in each of the one or more sample target histological images,
wherein the first set of patches is associated with the second set of patches in the predictive model,
wherein applying the one or more display characteristics comprises modifying a plurality of patches in the received histological image based on the second set of patches in the identified at least one target histological image,
wherein the first unsupervised learning model is trained based on one or more features associated with the target region in the histological image, and
wherein the identified at least one target histological image includes a staining image.

2. The method of claim 1, wherein identifying the target region corresponding to the candidate type of tissue comprises identifying a plurality of regions comprising the target region in the histological image,
wherein the predictive model comprises a first set of regions in each of the one or more sample histological images and a second set of regions in each of the one or more sample target histological images,
wherein the first set of regions is associated with the second set of regions in the predictive model, and
wherein applying one or more display characteristics comprises modifying the plurality of regions in the received histological image based on the second set of regions in the identified at least one target histological image.

3. The method of claim 1, wherein each of the first unsupervised learning model, the second unsupervised learning model, and the predictive model comprises a multilayer model defined by one or more model hyperparameters and one or more weights of an artificial neural network.

4. An image processing device for processing a histological image captured by a medical imaging device, the image processing device comprising:
- a storage;
- a communication unit; and
- a processor comprising a first autoencoder and an image generating unit,
- wherein the first autoencoder is configured to:
  - receive the histological image including at least one type of tissue;
  - determine a candidate type of tissue in the histological image;
  - identify a target region corresponding to the candidate type of tissue in the histological image; and
  - identify at least one target histological image corresponding to the target region in the histological image based on a predictive model associating one or more sample histological images with one or more sample target histological images,
  - apply one or more display characteristics associated with the identified at least one target histological image to the histological image; and
  - generate a modified image of the histological image including the applied one or more display characteristics,
- wherein a first unsupervised learning model is generated by training the first autoencoder of the processor based on a first set of sample histological images, and a second unsupervised learning model is generated by training a second autoencoder of the processor based on a second set of sample target histological images,
- wherein the predictive model is generated by associating the second unsupervised learning model with the first unsupervised learning model based on a set of matching images,
- wherein the set of matching images include M sample histological images in the first set of sample histological images and N sample target histological images in the second set of sample target histological images,
- wherein one or more anatomical locations of the M sample histological images in the first set of sample histological images are aligned to match one or more anatomical locations of the N sample target histological images in the second set of sample target histological images, M and N being positive integers,
- wherein the predictive model comprises data regarding one or more features indicative of at least one display characteristic and is trained by associating one or more features from the N sample target histological images with one or more features from the M sample histological images,
- wherein the predictive model comprises a first set of patches in each of the one or more sample histological images and a second set of patches in each of the one or more sample target histological images,
- wherein the first set of patches is associated with the second set of patches in the predictive model,
- wherein the image generating unit is further configured to modify a plurality of patches in the received histological image based on the second set of patches in the identified at least one target histological image,
- wherein the first unsupervised learning model is trained based on one or more features associated with the target region in the histological image, and
- wherein the identified at least one target histological image includes a staining image.

5. The image processing device of claim 4, wherein the first autoencoder is further configured to identify a plurality of regions comprising the target region in the histological image,
- wherein the predictive model comprises a first set of regions in each of the one or more sample histological images and a second set of regions in each of the one or more sample target histological images,
- wherein the first set of regions is associated with the second set of regions in the predictive model, and
- wherein the image generating unit is further configured to modify the plurality of regions in the received histological image based on the second set of regions in the identified at least one target histological image.

6. A non-transitory computer-readable storage medium comprising instructions for processing a histological image, the instructions causing a processor of a computer to perform operations comprising:
- receiving the histological image including at least one type of tissue;
- determining a candidate type of tissue in the histological image;
- identifying a target region corresponding to the candidate type of tissue in the histological image;
- identifying at least one target histological image corresponding to the target region in the histological image based on a predictive model associating one or more sample histological images with one or more sample target histological images;
- applying one or more display characteristics associated with the identified at least one target histological image to the histological image; and
- generating a modified image of the histological image including the applied one or more display characteristics,
- wherein a first unsupervised learning model is generated by training a first autoencoder of the processor based on a first set of sample histological images, and a second unsupervised learning model is generated by training a second autoencoder of the processor based on a second set of sample target histological images,
- wherein the predictive model is generated by associating the second unsupervised learning model with the first unsupervised learning model based on a set of matching images,
- wherein the set of matching images include M sample histological images in the first set of sample histological images and N sample target histological images in the second set of sample target histological images,
- wherein one or more anatomical locations of the M sample histological images in the first set of sample histological images are aligned to match one or more anatomical locations of the N sample target histological images in the second set of sample target histological images, M and N being positive integers,
- wherein the predictive model comprises data regarding one or more features indicative of at least one display characteristic and is trained by associating one or more features from the N sample target histological images with one or more features from the M sample histological images, wherein the predictive model comprises a first set of patches in each of the one or more sample histological images and a second set of patches in each of the one or more sample target histological images, wherein the first set of patches is associated with the second set of patches in the predictive model, wherein applying the one or more display characteristics comprises modifying a plurality of patches in the received histological image based on the second set of patches in the identified at least one target histological image, wherein the first unsupervised learning model is trained based on one or more features associated with the target region in the histological image, and wherein the identified at least one target histological image includes a staining image.

7. The medium of claim 6, wherein identifying the target region corresponding to the candidate type of tissue comprises identifying a plurality of regions comprising the target region in the histological image, wherein the predictive model comprises a first set of regions in each of the one or more sample histological images and a second set of regions in each of the one or more sample target histological images, wherein the first set of regions is associated with the second set of regions in the predictive model, and wherein applying one or more display characteristics comprises modifying the plurality of regions in the received histological image based on the second set of regions in the identified at least one target histological image.

* * * * *